United States Patent [19]

Barnette

[11] Patent Number: 4,479,901
[45] Date of Patent: Oct. 30, 1984

[54] FLUORINATION OF CARBANIONS WITH N-FLUORO-N-ALKYLSULFONAMIDES

[75] Inventor: William E. Barnette, Wilmington, Del.

[73] Assignee: E. I. Du Pont de Nemours and Company, Wilmington, Del.

[21] Appl. No.: 523,356

[22] Filed: Aug. 15, 1983

[51] Int. Cl.$^3$ .................... C07D 243/26; C07C 69/76; C07C 69/38; C07C 55/08; C07C 55/02; C07C 39/38; C07C 43/225
[52] U.S. Cl. ............................. 260/239 BD; 560/82; 560/83; 560/192; 562/489; 562/596; 564/91; 564/96; 568/348; 568/649; 568/737; 570/127; 570/134; 570/141
[58] Field of Search ...................... 564/91, 96; 560/82, 560/192; 568/348, 649, 737; 570/127, 134, 141; 562/489, 596; 260/239 BD

[56] References Cited

U.S. PATENT DOCUMENTS 4,232,016 11/1980 Poetsch et al. .............. 260/239 BD

OTHER PUBLICATIONS

Duniber et al., "The Addition of N,N-Dichlorosulfonamides to Unsaturates", *J. Org. Chem.*, vol. 33, No. 12, Dec. 1968, p. 4336.

Purrington et al., "1-Fluoro-2-pyridone: A Useful Flourinating Reagent", *J. Org. Chem.*, vol. 48, p. 761-2, Mar. 11, 1983.

*Primary Examiner*—Natalie Trousof
*Assistant Examiner*—Bruce D. Gray

[57] ABSTRACT

Process for fluorinating an organic carbanion, which process comprises contacting and reacting, in a dry inert atmosphere, the compound of the formula selected from

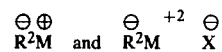

wherein

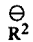

is the carbanion, M is a counter ion, and X is a halide and a selected N-flouro-N-alkylsulfonamide.

16 Claims, No Drawings

FLUORINATION OF CARBANIONS WITH N-FLUORO-N-ALKYLSULFONAMIDES

BACKGROUND OF THE INVENTION

1. Field of the Invention

This invention relates to the fluorination of carbanions with N-fluoro-N-alkylsulfonamides.

2. Background Information

N-Fluoro-N-alkylsulfonamides are known and their preparation by reaction of N-alkylsulfonamides with fluorine/inert-carrier-gas mixtures is disclosed in general terms in the art.

Barton et al., *JCS Perkin Trans.*, 1, 732 (1974); U.S. Pat. No. 3,917,688 and DE No. 2,332,430 all disclose processes for the preparation of N-fluoro-N-alkylsulfonamides by the reaction of sulfonamides with trifluoromethyl hypofluorite, according to the equation:

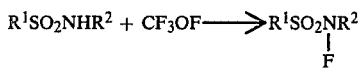

wherein $R^1$ and $R^2$ are hydrocarbyl groups or substituted hydrocarbyl groups. U.S. Pat. No. 3,917,688 further discloses that fluorine may be used in the preparation of N-fluoro-N-alkylsulfonamides, but that carefully controlled reaction conditions will generally be necessary to minimize the extent of unwanted side reactions. The fluorosulfonamides so obtained were further converted to biologically active fluoroamines.

Seguin et al., *J. Fluorine Chem.*, 15, 201 (1980) disclose the preparation of N-fluoro-N-alkylsulfonamides by the reaction of N-toluenesulfonyl aziridines with trifluoromethyl hypofluorite, according to the equation:

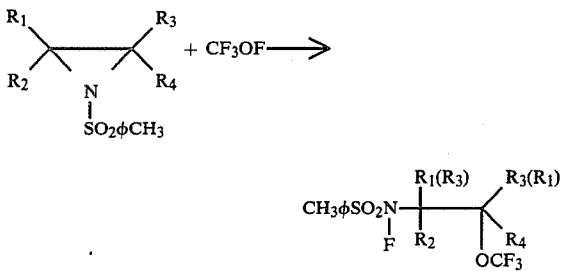

wherein $R^1$ is $CH_3$ and $R^2$, $R^3$ and $R^4$ are H or $CH_3$.

Grakauskas and Baum, *J. Org. Chem.*, 35, 1545 (1970) describe the preparation of N-fluoro-N-alkylcarboxamides by reaction of the N-alkylcarboxamide with fluorine/nitrogen mixtures at 0°–5° C., according to the equation:

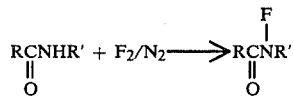

wherein R and R' are alkyl or substituted alkyl. No utility for the products is disclosed.

Grakauskas and Baum, *J. Org. Chem.*, 34, 2840 (1969) describe the preparation of N-fluoro-N-substituted carbamates by reaction of a carbamate with fluorine/nitrogen mixtures at 0° to −20° C., according to the equation:

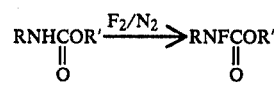

wherein R and R' are alkyl, substituted alkyl, or cycloalkyl. The products may be further converted to difluoroamino compounds.

The fluorination of carbanions by N-fluoro-N-alkylsulfonamides does not appear to be disclosed in the art. Fluorinations have been reported using N-fluoroperfluoropiperidine (FPFP), perchloryl fluoride or 1-fluoro-2-pyridone.

Banks and Williamson, *Chem. Ind.*, 1864 (1964) disclose the fluorination of sodium 2-nitropropanide (40% yield) and of sodium diethyl malonate (5% yield) by reaction with FPFP, according to the respective equations:

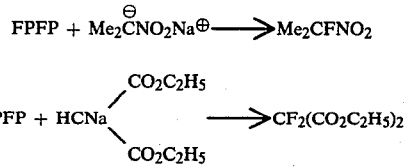

Polishchuk and German, *Tet. Lett.*, 5169 (1972) disclose the fluorination of sodium phenolate according to the equation:

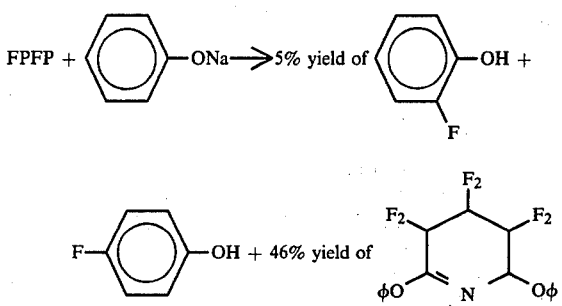

The use of perchloryl fluoride as a fluorinating agent for anions is reviewed by Sheppard and Sharts, *Org. React.*, 21, 225 (1974). Some typical examples include:

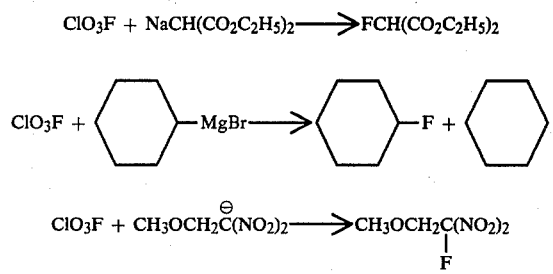

Purrington and Jones, *J. Org. Chem.*, 48, 761 (1983) disclose that 1-fluoro-2-pyridone fluorinates malonate anions, but in variable low yields, according to the equation:

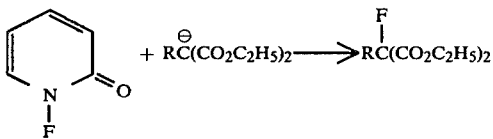

DETAILED DESCRIPTION OF THE INVENTION

This invention resides in the process for the fluorination at a carbon atom of a carbanion by treatment of the latter with an N-fluoro-N-alkylsulfonamide. The reaction proceeds according to the equation:

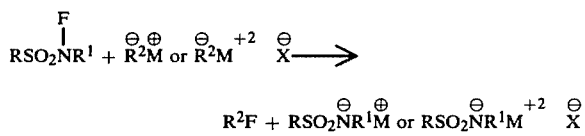

wherein

R is $C_{1-30}$ branched or straight chain alkyl, $C_{3-30}$ cycloalkyl, ar($C_{1-10}$ alkyl) or aryl wherein ar and aryl are $C_{6-14}$;

$R^1$ is $C_{1-30}$ branched or straight chain alkyl, $C_{3-30}$ cycloalkyl or ar($C_{1-10}$ alkyl) wherein ar is $C_{6-14}$;

$R^2$ is an organic carbanion, excluding β-diketo enolates and including but not limited to diester enolates, ester enolates, keto ester enolates, ketone enolates, nitronates, aryl and alkyl carbanions, acid enolates, amide enolates, naphtholates, and sulfur-, selenium- and phosphorus-stabilized carbanions;

$M^\oplus$ is an alkali metal or tetraalkylammonium cation;

$M^{+2}$ is an alkaline earth metal cation;

$X^\ominus$ is fluoride, chloride, bromide or iodide; and

F is $^{19}F$ or $^{18}F$.

It is to be understood that in the aforesaid definitions of R and $R^1$, "cycloalkyl" is intended to include bicycloalkyl groups, for example, 2-norbornyl.

The best conditions for carrying out the fluorination, that is, mode of addition, choice of solvent, choice of sulfonamide reagent, reaction temperature, mode of anion generation, and stoichiometry, are dependent upon the type of anion to be fluorinated and are summarized as follows:

1. Addition of a solution of the anion dropwise to a solution of the fluorosulfonamide generally provides the best yields but the inverse mode of addition also provides the same product.

2. Nonpolar hydrocarbon solvents, such as benzene, toluene, or hexane, are better reaction media than polar solvents, such as dimethylformamide, dimethoxyethane, tetrahydrofuran, or diethyl ether. However, for anion systems which cannot be generated in nonpolar solvents, preparation of the anion in a polar solvent followed by dilution with a nonpolar solvent and addition to the fluorosulfonamide in a nonpolar solvent is effective. Solvents which react with anions, such as methylene chloride and chloroform, are to be strictly avoided.

3. For strongly basic anions, such as alkyl and aryl organometallics, β-elimination of hydrogen fluoride from the N-fluoro-N-alkylsulfonamide reagent can become a major side reaction, reducing the yields of fluorination products. Use of a fluorosulfonamide wherein the tendency toward elimination has been reduced, for example, $R^1$ is 2-norbornyl or neopentyl, or eliminated, for example, $R^1$ is t-butyl, affords the best results. Use of a nonpolar solvent system also suppresses elimination.

4. The reaction temperature is selected from a consideration of the reactivity of the anion. Reactions with stabilized anions, such as diester enolates, are best carried out at about 0° to about 40° C. With more reactive anions, such as unstabilized enolates, reactions are best carried out at or below 0° C., preferably from about −50° to about −20° C. For highly reactive and strongly basic anions, such as alkyl and aryl lithium compounds, the best temperature range is about −78° to about 0° C.

5. Selection of the cationic counter ion $M^\oplus$ or $M^{+2}$ is not critical and is a matter of convenience. Cations of the alkali metals, for example, lithium, sodium and potassium, cations of the alkaline earth metals, for example, magnesium, and tetraalkylammonium salts react successfully.

6. One mole equivalent of fluorosulfonamide reacts with one mole equivalent of anion. Reducing the mole ratio of fluorosulfonamide to anion below 1:1 reduces the yield of desired product.

All reactions require a dry (moisture-free) inert (for example, nitrogen, argon or helium) atmosphere.

The invention herein also resides in compositions of matter for four N-alkyl-N-fluorosulfonamides, namely:

(1) N-fluoro-N-neopentyl-p-toluenesulfonamide;

(2) N-fluoro-N-(exo-2-norbornyl)-p-toluenesulfonamide;

(3) N-fluoro-N-(endo-2-norbornyl)-p-toluenesulfonamide; and (4) N-fluoro-N-neopentyl-n-butylsulfonamide.

N-Fluoro-N-alkylsulfonamides are prepared according to the equation:

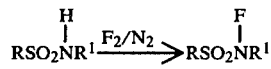

wherein R and $R^1$ are as defined above. An N-alkyl sulfonamide, readily synthesized using prior art technology from a sulfonyl halide and an alkyl amine, can be dissolved in fluorotrichloromethane or a mixture of fluorotrichloromethane and an inert chlorinated hydrocarbon solvent, such as chloroform or methylene chloride. Fluorine (as $^{19}F_2$ or $^{18}F^{19}F$), diluted with an inert gas, such as nitrogen, is then passed through the solution. The best results are obtained by passing a molar equivalent quantity of fluorine (about 1% to about 5% in nitrogen, volume/volume basis) into a solution of the sulfonamide in a 1:1 mixture of fluorotrichloro methane and chloroform at −78° C. through a vibrating mixer shaft while mixing. The sulfonamides of amines possessing a primary alkyl substituent give higher yields of the fluorosulfonamide than amines with secondary and tertiary alkyl groups. This results from the competing fluorination of the product fluorosulfonamide. The product N-fluoro-N-alkylsulfonamide can be isolated by column chromatography. Fluorosulfonamides wherein R is p-tolyl and $R^1$ is methyl, neopentyl, exo-2-norbornyl, endo-2-norbornyl, cyclohexyl, or t-butyl, and also wherein R is n-butyl and $R^1$ is neopentyl, have been prepared in this way. Yields of fluorosulfonamide range from 15% to 70%. Subject to the limitations described previously, all known N-fluoro-N-alkylsulfonamides, as well as the four novel sulfonamides noted above, perform equally well in the process of the invention.

Utility

N-Fluoro-N-alkylsulfonamides are useful as fluorinating agents, particularly in the fluorination of carbon anions. The fluorinated products from carbon anions are useful intermediates in the preparation of fluorinated agrichemicals and pharmaceuticals.

Fluorinated compounds which could be prepared by the process of the invention include:
Flurazepam (hypnotic),
Haloperidol (antipsychotic),
Difluorbenzuron (insecticide),
Fenisorex (anorectic),
Fluoroprop-isopropyl (herbicide), and
Flurbuprofen (anti-inflammatory).

The invention process also would be useful for the preparation of $^{18}F$-radio-labelled compounds having utility in positron emission transaxial tomography (PETT). The N-fluoro-N-alkylsulfonamide would be prepared using $^{18}F^{19}F$. Typical compounds which could be prepared include:
$^{18}F$-labelled haloperidol,
$^{18}F$-labelled 4-fluoroestrone,
$^{18}F$-labelled 6-fluoroglucose,
$^{18}F$-labelled 21-fluoroprogesterone, and
$^{18}F$-labelled 6-fluorotryptophan.

Treatment of the product of Example 11, infra, with methyl isocyanate would give 2-fluorocarbaryl. Carbaryl is a commercial insecticide sold under the trademark Sevin ®.

Preparation of the amide enolate of diazepam and treatment with an N-fluoro-N-alkylsulfonamide would yield 2-fluoro-diazepam. Diazepam is a commercial antidepressant sold under the trademark Valium ®.

The process of the invention is believed to be superior to fluorinating procedures known in the art for at least the following reasons:
(1) N-Fluoro-N-alkylsulfonamides are readily prepared in high yield (commonly used N-fluoroperfluoropiperidine (FPFP) electrochemically generated in 5% yield).
(2) N-Fluoro-N-alkylsulfonamides are stable, relatively non-toxic, and easily measured. (commonly used perchloryl fluoride is extremely toxic and gaseous).
(3) The use of N-fluoro-N-alkylsulfonamides gives high yields of fluorinated products, and the by-products are inert, readily separated sulfonamides. FPFP, in contrast, gives low yields; and perchloryl fluoride gives comparable yields but produces dangerously explosive reaction mixtures.
(4) The N-fluoro-N-alkylsulfonamides are more stable than 1-fluoro-2-pyridone and give higher yields of fluorination products.

In the following examples, temperatures are in degrees Celsius. Examples 1 to 4 relate to the preparation of the novel compounds of this invention; Experiments 1 to 3 relate to the preparation of known N-fluoro-N-alkylsulfonamides which are useful in the process of this invention; and Examples 5 to 15 relate to the process of this invention.

EXAMPLE 1

Preparation of
N-Fluoro-N-neopentyl-p-toluenesulfonamide

N-Neopentyl-p-toluenesulfonamide (2.41 g, 10 mmole) was dissolved in 1:1 fluorotrichloromethane-chloroform (450 mL) and the solution was cooled to $-78°$ under nitrogen. Fluorine (approximately 15 mmole, 5% in nitrogen) was bubbled into the solution through a vibrating mixer shaft for 2 h. The cold reaction mixture was poured into aqueous 10% potassium bicarbonate solution (200 mL) and the layers were separated. The organic phase was washed with aqueous 10% sodium thiosulfate (200 mL) and saturated sodium chloride (200 mL) solutions and dried over anhydrous magnesium sulfate. Filtration and removal of solvent under reduced pressure left a solid. Purification of the solid by flash column chromatography (silica, 25% methylene chloride in hexane) yielded N-fluoro-N-neopentyl-p-toluene-sulfonamide as a solid (1.47 g, 57% yield). This material, and additional samples prepared by this procedure, were analyzed and provided the following results: mp 58°–62.5°; IR (KBr) $\gamma_{max}$ (cm$^{-1}$) 3440 (b), 2980 (w), 1370 (m), 1175 (s), 734 (m); $^1$H NMR (80 MHz, CDCl$_3$) δ1.00 (s, 9H, C(CH$_3$)$_3$), 2.50 (s, 3H, CH$_3$), 3.00 (d, J=44 Hz, 2H, NCH$_2$), 7.40 (d, J=8 Hz, 2H, aromatic), 7.83 (d, J=8 Hz, 2H, aromatic); $^{19}$F NMR (94.1 MHz, CDCl$_3$) $-36.88$ (t, J=44 Hz, 1F, NF); HRMS calcd. for C$_{12}$H$_{18}$NO$_2$SF: 259.1042; found: 259.1029.

EXAMPLE 2

Preparation of
N-Fluoro-N-(exo-2-norbornyl)-p-toluenesulfonamide

N-(exo-2-Norbornyl)-p-toluenesulfonamide (5.3 g, 20 mmole) was dissolved in 1:1 fluorotrichloromethane-chloroform (450 mL) and the solution was cooled to $-78°$ under nitrogen. Fluorine (approximately 20 mmole, 1% in nitrogen) was bubbled into the solution through a vibrating mixer shaft for 4 h. The cold reaction mixture was poured into aqueous 10% potassium bicarbonate solution (200 mL) and the layers were separated. The organic phase was washed with aqueous 10% sodium thiosulfate (200 mL) and saturated sodium chloride (200 mL) solutions and dried over anhydrous magnesium sulfate. Filtration, removal of solvent under reduced pressure, and purification by flash column chromatography (silica, 20% methylene chloride in hexane) yielded N-fluoro-N-(exo-2-norbornyl)-p-toluenesulfonamide as a colorless oil which crystallized to a white solid (2.67 g, 47% yield) on standing. This material, and additional samples prepared by this procedure, were analyzed and provided the following results: mp 54°–60°; IR (KBr) $\gamma_{max}$ (cm$^{-1}$) 3440 (b), 2960 (w), 1375 (m), 1175 (s), 715 (m); $^1$H NMR (80 MHz, CDCl$_3$) δ0.975–2.17 (m, 8H), 2.3 (b, 1H), 2.47 (s, 3H, CH$_3$), 2.63 (b, 1H), 3.18 (dm, J=22.7 Hz, 1H, NCH), 7.38 (d, J=8 Hz, 2H, aromatic), 7.82 (d, J=8 Hz, 2H, aromatic); $^{19}$F NMR (94.1 MHz, CDCl$_3$) $-46.91$ (d, J=23 Hz, 1F, NF); HRMS calcd. for C$_{14}$H$_{18}$NO$_2$SF: 283.1042; found: 283.1057.

EXAMPLE 3

Preparation of
N-Fluoro-N-(endo-2-norbornyl)-p-toluenesulfonamide

The procedure of Example 2 was repeated except that N-(endo-2-norbornyl)-p-toluenesulfonamide was used. The yield of the desired product was 71%. Analytical results were as follows: mp 78°–81°; IR (KBr) $\gamma_{max}$ (cm$^{-1}$) 3440 (b), 2950 (w), 1595 (w), 1370 (m), 1170 (s); $^1$H NMR (80 MHz, CDCl$_3$) δ1.00–2.40 (m, 10H), 2.48 (s, 3H, CH$_3$), 3.32 (dm, J=14.6 Hz, 1H, NCH), 7.43 (d, J=8 Hz, 2H, aromatic), 7.85 (d, J=8 Hz, 2H, aromatic); $^{19}$F NMR (94.1 MHz, CDCl$_3$) −36.98 (d, J=15.5 Hz); HRMS calcd. for C$_{14}$H$_{18}$NO$_2$SF: 283.1042; found: 283.1045.

EXAMPLE 4

Preparation of N-Fluoro-N-neopentyl-n-butylsulfonamide

The procedure of Example 2 was repeated except that N-neopentyl-n-butylsulfonamide was used. The yield of the desired product was 50%. Analytical results were as follows: IR (liquid film) $\gamma_{max}$ (cm$^{-1}$) 2970 (s), 1370 (s), 1360 (s), 1160 (s); $^1$H NMR (80 MHz, CDCl$_3$) δ1.03 (m, 12H), 1.20-2.20 (m, 4H), 3.27 (d, J=42.7 Hz, 2H, NCH$_2$), 3.32 (m, 2H, CH$_2$SO$_2$); $^{19}$F NMR (94.1 MHz, CDCl$_3$) −38.40 (t, J=46 Hz); HRMS (M+1) calcd. for C$_9$H$_{21}$NO$_2$SF: 226.1276; found: 226.1280.

EXPERIMENTS 1 TO 3

The following additional N-fluorosulfonamides, known in the art, were prepared by the procedure of Example 1 or Example 2 (R and R$^1$ are from the formula RSO$_2$N(F)R$^1$):

| Expt. No. | R | R$^1$ | % F$_2$ | % Yield |
|---|---|---|---|---|
| 1 | p-tolyl | methyl | 1 | 59 |
| 2 | p-tolyl | t-butyl | 5 | 14 |
| 3 | p-tolyl | cyclohexyl | 5 | 11 |

Analytical data for Experiments 1 to 3 are provided below.

EXPERIMENT 1

Preparation of N-Fluoro-N-methyl-p-toluenesulfonamide mp=42°-44°; IR (KBr) $\gamma_{max}$ (cm$^{-1}$) 3430 (b), 1595 (w), 1370 (s), 1190 (s), 1180 (s); $^1$HNMR (80 MHz, CDCl$_3$) δ2.50 (s, 3H, CH$_3$), 3.15 (d, J=32 Hz, 3H, NCH$_3$), 7.42 (d, J=8 Hz, 2H, aromatic), 7.85 (d, J=8 Hz, 2H, aromatic); $^{19}$F NMR (94.1 MHz, CDCl$_3$) −37.62 (q, J=31.5 Hz); HRMS calcd. for C$_8$H$_{10}$NO$_2$SF: 203.0416; found: 203.0463.

EXPERIMENT 2

Preparation of N-Fluoro-N-t-butyl-p-toluenesulfonamide mp 59°-62.5°; IR (KBr) $\gamma_{max}$ (cm$^{-1}$) 3430 (b), 2895 (w), 1595 (w), 1365 (s), 1165 (s); $^1$H NMR (80 MHz, CDCl$_3$) δ1.43 (d, J=2.7 Hz, 9H, C(CH$_3$)$_3$), 2.45 (s, 3H, CH$_3$), 7.33 (d, J=8 Hz, 2H, aromatic), 7.87 (d, J=8 Hz, 2H, aromatic); $^{19}$F NMR (94.1 MHz, CDCl$_3$) −62.78 (m); HRMS calcd. for C$_{11}$H$_{16}$NO$_2$SF: 245.0885; found: 245.0081.

EXPERIMENT 3

Preparation of N-Fluoro-N-cyclohexyl-p-toluenesulfonamide

IR (liquid film) $\gamma_{max}$ (cm$^{-1}$) 2940 (m), 1595 (w), 1370 (m), 1345 (m), 1170 (s); $^1$H NMR (80 MHz, CDCl$_3$) δ0.75-2.30 (m, 10H), 2.40 (s, 3H, CH$_3$), 3.63 (dm, J=32 Hz, 1H, NCH), 7.31 (d, J=8 Hz, 2H, aromatic), 7.82 (d, J=8 Hz, 2H, aromatic); $^{19}$F NMR (94.1 MHz, CDCl$_3$) −71.63 (d, J=32 Hz); HRMS calcd for C$_{13}$H$_{18}$NO$_2$SF: 271.1042; found: 271.1027.

EXAMPLE 5

Preparation of Diethyl 2-fluoro-2phenylmalonate

Diethyl phenylmalonate (472 mg, 431 μL, 2 mmole) was dissolved in anhydrous tetrahydrofuran (10 mL) under nitrogen. Sodium hydride (96 mg as a 60% oil dispersion, 2.4 mmole) was added and the mixture was stirred until hydrogen evolution ceased (about 15 minutes). The solution was then cooled to −50° under nitrogen and N-fluoro-N-neopentyl-p-toluenesulfonamide (518 mg, 2 mmole, as prepared in Example 1) was added and the mixture was stirred at −50° for 15 minutes. The solution was stirred at −20° for 15 minutes, 0° for 15 minutes, and room temperature for 15 minutes before being diluted with ether (100 mL). The ether solution was washed with aqueous 1N oxalic acid (30 mL), 10% aqueous potassium bicarbonate (30 mL), and saturated aqueous sodium chloride (30 mL) solutions, and then dried over anhydrous magnesium sulfate. Filtration, removal of solvent under reduced pressure, and purification by flash column chromatography (silica, 30% methylene chloride in hexane) yielded diethyl 2-fluoro-2-phenylmalonate (410 mg, 81% yield) as a colorless oil. This material, and additional samples prepared by this procedure, were analyzed and provided the following results: IR (liquid film) $\gamma_{max}$ (cm$^{-1}$) 2800 (m), 1760 (s, ester), 1420 (m), 1350 (m), 1250 (s); $^1$H NMR (80 MHz, CDCl$_3$) δ1.32 (t, J=8.0 Hz, 6H, CH$_3$), 4.33 (q, J=8 Hz, 4H, CH$_2$), 7.50 (m, 5H); $^{19}$F NMR (94.1 MHz, CDCl$_3$) −162.23; HRMS calcd. for C$_{13}$H$_{15}$O$_4$F: 254.0954; found: 254.0947.

EXAMPLE 6

Preparation of Diethyl 2-fluoro-2-methylmalonate

Diethyl 2-methylmalonate (870 mg, 860 μL, 5 mmole) was dissolved in anhydrous tetrahydrofuran (10 mL) under nitrogen. Sodium hydride (250 mg as a 60% oil dispersion, 6 mmole) was added and the mixture was stirred until hydrogen evolution ceased (about 15 minutes). The reaction mixture was diluted with toluene (20 mL) and transferred dropwise to a solution of N-fluoro-N-neopentyl-p-toluenesulfonamide (1.295 g, 5 mmole) in anhydrous toluene (10 mL) over 5 minutes. A precipitate formed during addition and the reaction temperature rose from 23° to 36°. After stirring an additional 5 minutes under nitrogen, the reaction mixture was diluted with ether (100 mL), washed with aqueous 1N oxalic acid (30 mL), 10% aqueous potassium bicarbonate (30 mL), and saturated aqueous sodium chloride (30 mL) solutions, and then dried over anhydrous magnesium sulfate. Filtration, removal of solvent under reduced pressure, and purification by flash column chromatography (silica, 1:1 methylene chloride-hexane) yielded diethyl 2-fluoro-2-methylmalonate (512 mg, 53% yield) as a colorless liquid. This material, and additional samples prepared by this procedure, were analyzed and provided the following results: IR (liquid film) $\gamma_{max}$ (cm$^{-1}$) 2940 (m), 1750 (s, ester), 1440 (m), 1370 (m), 1290 (s); $^1$H NMR (80 MHz, CDCl$_3$) δ1.33 (t, J=8 Hz, 6H, CH$_2$CH$_3$), 1.81 (d, J=22.67 Hz, 3H, CH$_3$), 4.30 (q, J=8 Hz, 4H, CH$_2$); $^{19}$F NMR (94.1 MHz, CDCl$_3$) −158.02 (q, J=22 Hz, 1F); HRMS (M—CH$_2$CH$_3$) calcd. for C$_6$H$_8$O$_3$F: 147.0457; found: 147.0450; LRMS (CI) m/e 193.

EXAMPLE 7

Preparation of Fluorobenzene

N-Fluoro-N-t-butyl-p-toluenesulfonamide (123 mg, 0.5 mmole) was dissolved in anhydrous ether (1 mL) under nitrogen. Phenylmagnesium bromide (170 μL of a 3.0M solution in ether) was added dropwise and the mixture was stirred at room temperature under nitrogen. After 10 minutes acetic acid (100 μL) was added to quench the reaction. Diethyl 2-fluoro-2-phenylmalonate (34.8 mg) was added as internal standard and the yield of fluorobenzene was determined to be 50% by $^{19}F$ NMR. $^{19}F$ NMR (94.1 MHz, diethyl ether) −113.43.

EXAMPLE 8

Preparation of 2-Fluoro-1-naphthol

Potassium hydride (93.6 mg as a 35% oil dispersion, 0.82 mmol) was suspended in anhydrous tetrahydrofuran (2.5 mL) under nitrogen. 1-Naphthol (72 mg, 0.5 mmole) was added and the mixture was stirred until hydrogen evolution ceased (about 5 minutes) to produce potassium naphtholate. N-Fluoro-N-t-butyl-p-toluenesulfonamide (122 mg, 0.5 mmole) was dissolved in anhydrous tetrahydrofuran (2.5 mL) and the solution was added dropwise to the potassium naphtholate. After 20 minutes the reaction mixture was diluted with ether (100 mL), washed with aqueous 1N oxalic acid solution (30 mL), water (30 mL), and saturated aqueous sodium chloride solution (30 mL), and then dried over anhydrous magnesium sulfate. Filtration, removal of solvent under reduced pressure, and purification by flash column chromatography (silica, 25% methylene chloride in hexane) yielded 2-fluoro-1-naphthol (49 mg, 60% yield) as a white crystalline solid. This material, and an additional sample prepared by this procedure, were analyzed and provided the following results: $^1H$ NMR (90 MHz, CDCl$_3$) δ5.58 (b, 1H, OH), 7.00–8.30 (m, 6H, aromatic); $^{19}F$ NMR (94.1 MHz, CDCl$_3$) −146.78(m); HRMS calcd. for $C_{10}H_7OF$: 162.0480; found: 162.0439.

EXAMPLE 9

Preparation of N-t-Butyl-(2-fluoro-4-methyl)phenylsulfonamide

N-t-butyl-p-toluenesulfonamide (215 mg, 1 mmole) was dissolved in anhydrous tetrahydrofuran (3 mL) and the solution was cooled to −10° under nitrogen. n-Butyllithium (1.6 mL of a 1.25M solution in n-hexane) was added dropwise and the solution was allowed to warm to room temperature while stirring under nitrogen. The solution was then added dropwise to a solution of N-fluoro-N-(exo-2-norbornyl)-p-toluenesulfonamide (283 mg, 1 mmole) in anhydrous toluene (6 mL) under nitrogen. After 15 minutes the reaction mixture was diluted with ether (100 mL), washed with aqueous 1N oxalic acid (30 mL), 10% aqueous potassium bicarbonate (30 mL), and saturated aqueous sodium chloride (30 mL) solutions, and then dried over anhydrous magnesium sulfate. Filtration, removal of solvent under reduced pressure, and purification by flash column chromatography (silica, 20% ether in hexane) yielded N-t-butyl-(2-fluoro-4-methyl)phenylsulfonamide (127 mg, 52% yield) as a white solid; mp=110°–115°; IR (KBr) $\gamma_{max}$ (cm$^{-1}$) 3295 (s), 1328 (s), 1163 (s), 1140 (s), 1080 (m), 1010 (m); $^1H$ NMR (80 MHz, CDCl$_3$) δ1.23 (s, 9H, C(CH$_3$)$_3$), 2.43 (s, 3H, CH$_3$), 4.83 (b, 1H, NH), 7.00 (d, J=6.7 Hz, 1H, aromatic), 7.10 (m, 1H, aromatic), 7.83 (t, J=8.0 Hz, 1H, aromatic); $^{19}F$ NMR (94.1 MHz, CDCl$_3$) −112.44 (dd, J=11, 7.5 Hz); HRMS (M—CH$_3$) calcd. for $C_{10}H_{13}NO_2SF$: 230.0651; found: 230.0642.

EXAMPLE 10

Preparation of 3-Fluoroveratrole

Veratrole (690 mg, 640 μL, 5 mmole) was dissolved in anhydrous tetrahydrofuran (5 mL) under nitrogen. n-Butyllithium (4.6 mL of a 1.3M solution in n-hexane) was added dropwise and the mixture was stirred at room temperature under nitrogen. After 3 h the mixture was added dropwise to a solution of N-fluoro-N(exo-2-norbornyl)-p-toluenesulfonamide (1.415 g, 5 mmole) in anhydrous toluene (10 mL) under nitrogen. The internal temperature of the reaction rose from 25° to 53° during the addition. After stirring for 15 minutes the mixture was diluted with ether (100 mL), washed with aqueous 1N oxalic acid (30 mL), 10% aqueous potassium bicarbonate (30 mL), and saturated aqueous sodium chloride (30 mL) solutions, and then dried over anhydrous magnesium sulfate. Filtration, removal of solvent under reduced pressure, and purification by flash column chromatography (silica, 1:1 methylene chloride-hexane) yielded 3-fluoroveratrole (185 mg, 24% yield) as a colorless liquid. IR (liquid film) $\gamma_{max}$ (cm$^{-1}$) 2850 (w), 1620 (m), 1580 (m), 1500 (s), 1440 (s), 1250 (m), 1090 (s); $^1H$ NMR (80 MHz, CDCl$_3$) δ3.90 (s, 3H, CH$_3$), 3.95 (d, J=0.8 Hz, 3H, CH$_3$), 6.50–7.30 (m, 3H, aromatic); $^{19}F$ NMR (94.1 MHz, CDCl$_3$) −131.22 (m); HRMS calcd. for $C_8H_9O_2F$: 156.0586; found: 156.0565.

EXAMPLE 11

Preparation of 2-Fluoro-3,3,5,5-tetramethylcyclohexanone

Enol acetate (588 mg, 630 μL, 3 mmole) was added dropwise to a solution of methyllithium (4.6 mL of a 1.3M solution in ether) in anhydrous ether (5 mL) previously cooled to 0° under nitrogen. After stirring 10 minutes the solution was cooled to −78° under nitrogen, diluted with anhydrous toluene (10 mL), and transferred dropwise over 15 minutes to a solution of N-fluoro-N-(exo-2-norbornyl)-p-toluenesulfonamide (849 mg, 3 mmole) in anhydrous toluene (5 mL) previously cooled to −78°. The solution was stirred at −78° for 1 h, then at −20° for 4 h. The reaction mixture was then diluted with ether (100 mL), washed with aqueous 1N oxalic acid (30 mL), 10% aqueous potassium bicarbonate (30 mL), and saturated aqueous sodium chloride (30 mL) solutions, and then dried over anhydrous magnesium sulfate. Filtration, removal of solvent under reduced pressure, and purification by flash column chromatography (silica, 75% methylene chloride in hexane) yielded 2-fluoro-3,3,5,5-tetramethylcyclohexanone (180 mg, 35% yield) as a colorless liquid which crystallized on standing. This material, and additional samples prepared by this procedure, were analyzed and provided the following results: mp 27°–31°; IR (liquid film) $\gamma_{max}$ (cm$^{-1}$) 2840 (s), 1700 (s, CO), 1430 (s), 1330 (s), 1150 (s); $^1H$ NMR (80 MHz, CDCl$_3$) δ0.83–1.33 (m, 12H, CH$_3$), 1.70 (b, 2H, CH$_2$), 2.23 (d, J=10 Hz, 1H, CHCO), 2.38 (d, J=10 Hz, 1H, CHCO), 4.61 (d, J=49.3 Hz, 1H, CHF); $^{19}F$ NMR (94.1 MHz, CDCl$_3$) −199.14 (d, 49 Hz); HRMS calcd. for $C_{10}H_{17}OF$: 172.1263; found: 172.1266.

EXAMPLE 12

Preparation of 1-Fluorotetradecane

Tetradecylmagnesium bromide (2.5 mmole) was prepared from tetradecyl bromide (692 mg, 740 μL, 2.5 mmole) and magnesium (120 mg, 5 mmole) in anhydrous ether (5 mL) under nitrogen. The mixture was diluted with anhydrous toluene (10 mL) and transferred dropwise over 5 minutes to a solution of N-fluoro-N-(exo-2-norbornyl)-p-toluenesulfonamide (707 mg, 2.5 mmole) in anhydrous toluene (5 mL) previously cooled to −78° under nitrogen. The resulting mixture was stirred at −78° for 30 minutes and then slowly allowed to warm to room temperature over 30 minutes. The reaction mixture was then diluted with ether (100 mL), washed with aqueous 1N oxalic acid (30 mL), 10% aqueous potassium bicarbonate (30 mL), and saturated aqueous sodium chloride (30 mL) solutions, and then dried over anhydrous magnesium sulfate. Filtration, removal of solvent under reduced pressure, and purification by flash column chromatography (silica, pentane to methylene chloride) yielded pure 1-fluorotetradecane (20 mg) and an additional sample (90 mg) contaminated with 1-bromotetradecane. Further purification of the 90 mg mixture by preparative layer chromatography (silica, pentane) yielded pure 1-fluorotetradecane (60 mg); total 80 mg, 15% yield. IR (liquid film) $\gamma_{max}$ (cm$^{-1}$) 2955 (m), 2925 (s), 2855 (m), 1460 (m); $^1$H NMR (80 MHz, CDCl$_3$) δ0.88 (t, J=5.3 Hz, 3H, CH$_3$), 1.00–2.40 (m, 24H), 4.42 (dt, J=48, 6.7 Hz, 2H, CH$_2$F); $^{19}$F NMR (94.1 MHz, CDCl$_3$) −218.81 (tt, J=47.5, 23.5 Hz); HRMS calcd. for C$_{14}$H$_{29}$F: 216.2254; found: 216.2249.

EXAMPLE 13

Preparation of 2-Fluoro-2-nitropropane

N-Fluoro-N-t-butyl-p-toluenesulfonamide (490 mg, 2 mmole) was dissolved in anhydrous toluene (1.6 mL) and the solution was cooled to −20° under nitrogen. Tetra-n-butylammonium-2-nitropropanide (3.4 mL of a 0.6M solution in benzene) was added dropwise over 5 minutes and the mixture was stirred at −20° under nitrogen. After 4 h the mixture was warmed to room temperature, stirred an additional 30 minutes, and then the reaction was quenched by addition of acetic acid (115 μL). Gas chromatographic analysis indicated an 87% yield of 2-fluoro-2-nitropropane. o-Fluoroanisole (111.4 mg) was added as an internal standard and the yield was determined to be 85% by $^{19}$F NMR. $^{19}$F NMR (94.1 MHz, toluene-benzene) −112.38 (m).

EXAMPLE 14

Preparation of Diethyl 2-fluoro-2-phenylmalonate

Diethyl phenylmalonate (708 mg, 650 μL, 3 mmole) was dissolved in anhydrous tetrahydrofuran (5 mL) under nitrogen. Sodium hydride (144 mg as a 60% oil dispersion, 3.6 mmole) was added and the mixture was stirred until hydrogen evolution ceased (about 15 minutes). The solution was then diluted with anhydrous toluene (10 mL) and added dropwise to a solution of N-fluoro-N-neopentyl-n-butylsulfonamide (675 mg, 3 mmole) in anhydrous toluene (5 mL) and the mixture was stirred at room temperature under nitrogen. After 30 minutes the reaction mixture was diluted with ether (100 mL), washed with aqueous 1N oxalic acid (30 mL), 10% aqueous potassium bicarbonate (30 mL), and saturated aqueous sodium chloride (30 mL) solutions, and then dried over anhydrous magnesium sulfate. Filtration, removal of solvent under reduced pressure, and purification by flash column chromatography (silica, 1:1 methylene chloride-hexane) yielded diethyl 2-fluoro-2-phenylmalonate as a colorless liquid (508 mg). $^1$H NMR was consistent with the desired structure.

EXAMPLE 15

Preparation of N-Methyl-2-fluorodemoxepam

Potassium hydride (0.34 g as a 35% oil dispersion, 3.0 mmole) was cooled to −20° under nitrogen. N-Methyldemoxepan (750 mg, 2.5 mmole) was dissolved in anhydrous tetrahydrofuran (10 mL); the solution was cooled to −20° under nitrogen and then added rapidly to the potassium hydride. The mixture was stirred at −20° until hydrogen evolution ceased (about 30 minutes). The resulting cherry red solution was diluted with anhydrous toluene (20 mL) and then added dropwise over 15 minutes to a solution of N-fluoro-N-(exo-2-norbornyl)-p-toluenesulfonamide (1.06 g, 3.75 mmole) in anhydrous toluene (10 mL) at −50°. The mixture was stirred at −50° for 30 minutes and then the reaction was quenched at −50° by addition of aqueous 1N oxalic acid solution (50 mL). The reaction mixture was diluted with ether (100 mL) and the layers were separated. The organic phase was washed with 10% aqueous potassium bicarbonate (50 mL) and saturated aqueous sodium chloride (50 mL) solutions, and then dried over anhydrous magnesium sulfate. Filtration, removal of solvent under reduced pressure, and purification by flash column chromatography (silica, 2:1 methylene chloride to methylene chloride-ether) yielded the desired product as a white solid (415 mg, 52% yield). This material, and additional samples prepared by this procedure, were analyzed and provided the following results: mp 190.5°–194°; $^1$H NMR (80 MHz, CDCl$_3$) δ3.53 (s, 3H, NCH$_3$), 5.87 (d, J=48 Hz, 1H, CHF), 7.00–8.00 (m, 8H, aromatic); $^{19}$F NMR (94.1 MHz, DMSO) −177.04 (d, J=45 Hz); HRMS calcd. for C$_{16}$H$_{12}$N$_2$O$_2$ClF: 318.0571; found: 318.0576.

BEST MODE FOR CARRYING OUT THE INVENTION

The best mode presently contemplated for carrying out the invention is demonstrated in Example 15.

I claim:

1. Process for fluorinating an organic carbanion, which process comprises contacting and reacting, in a dry inert atmosphere, the compound of the formula selected from

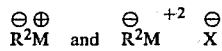

and the N-fluoro-N-alkylsulfonamide of the formula

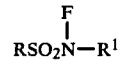

wherein
R is C$_{1-30}$ branched or straight chain alkyl, C$_{3-30}$ cycloalkyl, ar(C$_{1-10}$ alkyl) or aryl wherein ar and aryl are C$_{6-14}$;
R$^1$ is C$_{1-30}$ branched or straight chain alkyl, C$_{3-30}$ cycloalkyl or ar(C$_{1-10}$ alkyl) wherein ar is C$_{6-14}$;

$\overset{\ominus}{R^2}$ is an organic carbanion other than a β-diketo enolate;
M⊕ is an alkali metal or tetraalkylammonium cation;
M⁺² is an alkaline earth metal cation;
X⊖ is fluoride, chloride, bromide or iodide; and
F is ¹⁹F or ¹⁸F.

2. Process of claim 1 wherein the contacting and reacting are carried out at −78° to 0° C.

3. Process of claim 1 wherein the contacting and reacting are carried out at about 0° to 40° C.

4. Process of claim 1 wherein the compound is $\overset{\ominus}{R^2}\overset{\oplus}{M}$ wherein M⊕ is alkali metal.

5. Process of claim 1 wherein the compound is $\overset{\ominus}{R^2}\overset{+2}{M}\overset{\ominus}{X}.$ 6. Process of claim 1 wherein the mole ratio of alkylsulfonamide to carbanion $\overset{\ominus}{R^2}$ is about 1:1.

7. Process of claim 1 wherein there is present an inert solvent.

8. Process of claim 7 wherein the inert solvent is a nonpolar solvent.

9. Process of claim 7 wherein the inert solvent is a polar solvent.

10. Process of claim 8 wherein the solvent is selected from toluene, benzene and hexane.

11. Process of claim 9 wherein the solvent is selected from diethyl ether, tetrahydrofuran and dimethoxyethane.

12. Process of claim 1 wherein F is ¹⁸F.

13. N-Fluoro-N-neopentyl-p-toluenesulfonamide.

14. N-Fluoro-N-(exo-2-norbornyl)-p-toluenesulfonamide.

15. N-Fluoro-N-(endo-2-norbornyl)-p-toluenesulfonamide.

16. N-Fluoro-N-neopentyl-n-butylsulfonamide.

* * * * *